United States Patent
Yang et al.

(10) Patent No.: US 10,182,998 B2
(45) Date of Patent: *Jan. 22, 2019

(54) BENZENESULFONAMIDE COMPOSITIONS FOR TREATMENT OF MALIGNANT PLEURAL EFFUSIONS

(71) Applicant: GONGWIN BIOPHARM HOLDINGS CO., LTD., Taipei (TW)

(72) Inventors: Chuan-Ching Yang, Taipei (TW); Mao-Yuan Lin, Taipei (TW)

(73) Assignee: Gongwin Biopharm Holdings Co., Ltd., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 15/614,412

(22) Filed: Jun. 5, 2017

(65) Prior Publication Data

US 2017/0354622 A1     Dec. 14, 2017

Related U.S. Application Data

(63) Continuation-in-part of application No. 15/179,153, filed on Jun. 10, 2016, now Pat. No. 9,668,990.

(51) Int. Cl.
*A61K 31/18* (2006.01)
*A61K 9/20* (2006.01)

(52) U.S. Cl.
CPC ............ *A61K 31/18* (2013.01); *A61K 9/2004* (2013.01)

(58) Field of Classification Search
None
See application file for complete search history.

(56) References Cited

U.S. PATENT DOCUMENTS

| 5,891,454 A | 4/1999 | Wu et al. |
| 6,471,974 B1 | 10/2002 | Rees et al. |
| 2003/0022843 A1* | 1/2003 | Wu .......................... A61K 31/18 514/23 |
| 2005/0004142 A1* | 1/2005 | Adams ................. C07D 491/04 514/260.1 |
| 2005/0281822 A1* | 12/2005 | Cedarbaum ............ C07K 14/71 424/145.1 |
| 2014/0378466 A1 | 12/2014 | Maderna et al. |

FOREIGN PATENT DOCUMENTS

| CN | 101485644 A | 7/2009 |
| CN | 101940708 A | 1/2011 |
| CN | 104056104 A | 9/2014 |
| CN | 105267751 A | 1/2016 |
| CN | 105311599 A | 2/2016 |
| CN | 104922528 A | 6/2016 |

OTHER PUBLICATIONS

Gao et al., J. Thorac Dis, 2013, 5(4), pp. 472-83.*
Pignon et al., "Chemotherapy after surgery for early stage non-small cell lung cancer" (2015) retieved Sep. 11, 2017 from the internet at url: http://www.cochrane.org/CD011430/LUNGCA_chemotherapy-after-surgery-for-early-stage-non-small-cell-lung-cancer.*
Sartinin et al., Journal of Medicinal Chemistry (2014), 57(4), 1225-1235.*
Machine translation of CN 101485644, 2008.
Gao, "Antitumor Effect of Para-Toluenesulfonamide Against Lung Cancer Xeongraft in a Mouse Model", State Key Laboratory of Respiratory Disease; Beijing Vision Drugs Development Limited, Beijing China, Aug. 28, 2013, 472-483.
Singh, et al., "Dosage Forms: Non Parenteral", Encyclopedia of Pharmaceutical Technology, Marcel Dekker, Inc., 2008.
Form PCT/ISA/210, International Search Report dated Sep. 8, 2017, for PCT/US17/37015.

* cited by examiner

*Primary Examiner* — Karl J Puttlitz
(74) *Attorney, Agent, or Firm* — Kramer Amado P.C.

(57) ABSTRACT

The present disclosure provides a novel pharmaceutical composition for treating a malignant pleural effusion (MPE), including a benzenesulfonamide derivative and a pharmaceutically acceptable excipient. The present disclosure further provides a method for treating MPE by using the pharmaceutical composition.

11 Claims, No Drawings

BENZENESULFONAMIDE COMPOSITIONS FOR TREATMENT OF MALIGNANT PLEURAL EFFUSIONS

This application is a continuation-in-part application of U.S. patent application Ser. No. 15/179,153 filed Jun. 10, 2016, which is hereby incorporated by reference for all purposes as if fully set forth herein.

BACKGROUND OF THE INVENTION

1. Field of the Invention

The present disclosure relates to a method for treating malignant pleural effusions (MPE) in a subject, particularly for treating MPE in a subject suffering from lung cancer, breast cancer, lymphoma, leukemia, or mesothelioma in a late stage by a novel pharmaceutical composition comprising benzenesulfonamides. The present disclosure also relates to a pharmaceutical composition comprising benzenesulfonamides and a process for preparation thereof.

2. Description of Related Art

Cancers with various origins have been serious diseases worldwide. The later stage of cancer is diagnosed, the lower cure rate is. Malignant pleural effusions (MPE) resulted from metastatic malignant pleural tumors or primary malignant pleural tumors is one of the most common complication of malignant tumors. It is reported that 24% to 50% of exudative pleural effusions originated from malignant lesions and 50% of tumor metastasis finally lead to MPE. Top three MPE generating cancers are lung cancer the first, breast cancer the second, and lymphoma the third. The primary cancer tumor lesions have not been observed in about 5% to 10% of MPE cases. All malignant tumors excluding primary brain tumor and limbs tumor may generate MPE (*Am J Respir Crit Care Med Vol.* 162. P. 1987-2001, 2000).

MPE is often regarded as a complication in the late stage of tumors. MPE is rapidly developing and often complicated with the symptoms such as chest tightness, shortness of breath, palpitations, and unable supine. Delaying the treatment of MPE might cause barriers of respiration and circulation, hypoproteinemia, and anemia, and the severe symptoms might be life-threatening. Therefore, rapidly and effectively treating MPE is an important step in cancer therapy. However, the treatment of MPE is difficult due to high mortality rate. The one, three and six-month(s) mortality rates of patients with MPE are 50%, 60%, and 82%, respectively. The average life expectancy is merely 3.1 months. Effectively managing MPE has been one of the difficult issues in clinical treatments.

In clinical practice, removing pleural effusions and preventing its accumulation again, relieving symptoms, raising life quality, as well as extending survival period are the current main treatments for MPE. The major methods include chest drainage, video-assisted thoracic surgery (VATS), intrathoracic administration, pleural fixation, whole body chemotherapy, radiotherapy, thermal therapy and the like. However, limitation exists in each treatment application which results in limited therapy efficacy. Recently hyperthermic pleural perfusion treatment provides a new method and it is theoretically and technically supported. There are two kinds of hyperthermic pleural perfusion treatments: one is physiological saline, which exhibits low timeliness to pleural effusions control and high recurrence; the other is chemotherapy by cisplatin and so on, which is used for local anti-cancer and promoting pleural connection. However, over pleural connections are frequently observed in clinical practice, resulting in fibrin depositing on pleura, pleural capillaries and fibroblasts extending into fibrin and forming granulation tissue, gradually thickening to dense envelope and forming pleural fibreboard. The wide and rigid fibreboard wraps around the lung tissue and lacks flexibility, so as to limit chest expansion, severely reduce breath and increase the recurrence rate of pleural effusions. As a result, a pleural perfusion liquid effectively improving function of respiratory system and reducing recurrence rate remains a need yet to be met.

MPE is a secondary symptom of primary tumor. Therefore, the attention of clinical study and the improvement of treatment are relatively limited compared to other mainstream domains of tumor study. Meanwhile, the commercial profit is also limited. In view of the above problem of the conventional art, the technical purpose of the present disclosure is to provide a new medication with assured effect and fewer side effects to treat MPE. The study on MPE by benzenesulfonamides is so far underreported.

Chinese Patent Application No. 201010284152.0 discloses a Chinese medicine for treating MPE comprising the following Chinese herbs: *Codonopsis pilosula* 13-18 g, *Astragalus membranaceus* 28-32 g, prepared rhizome of *Rehmannia glutinosa* 13-18 g, *Angelica sinensis* 13-18 g, *Fritillaria cirrhosa* 8-12 g, *Wolfiporia extensa* 13-18 g, *Semen* 8-12 g, licorice 8-12 g, Chenpi 8-12 g, *Trichosanthes kirilowii* Maxim. 13-18 g, grifola 8-12 g, *Rhioma alismatis* 8-12 g, the root of *Paris polyphylla* 8-12 g, *Solanum lyratum* 8-12 g.

Chinese Patent Application No. 201410315790.2 discloses a medical composition for treating MPE comprising the following Chinese herbs: *Jacobinia suberecta* 20-30 parts, herb of *Villosulous veronicastrum* 9-15 parts, *Potentillae parvifoliae* fisch 5-15 parts, *Iris japonica* 25-30 parts, *Wusuli dragonflyorchis* rhizome 10-16 parts, *Phaenosperma globosa* 15-25 parts, *Chorion ovi* 3-8 parts, root of *Dunn Antictrema* 7-10 parts, *Manyflower solomonseal* rhizome 10-15 parts, *Paris polyphylla* 15-25 parts, *Solanum lyratum* 20-25 parts, *Duchesnea indica* 15-20 parts.

Chinese Patent Application No. 201510413494.0 discloses a medical composition for treating MPE comprising the following Chinese herbs: *Panax quinquefolius* 2-18 parts, *Panax pseudo-ginseng* 4-30 parts, *Semen lepidii* 2-18 parts, *Pyrosla lingua* 3-21 parts, *Zanthoxylum bungeanum* Maxia. 2-8 parts, *Cynanchi paniculati* 10-50 parts, *Trichosanthes kirilowii* Maxim., 5-25 parts, fresh *Astragalus* 10-50 parts, *Rhizoma alismatis* 2-18 parts, *Atractylodes macrocephalae* 3-21 parts, *Ziziphus jujuba* Mill. 2-12 parts.

Chinese Patent Application No. 201510776648.2 discloses a medication for treating chi yin deficiency type MPE, comprising *Codonopsis pilosula*, *Eleutherococcus senticosus*, *Scrophularia ningpoensis* Hemsl., *Plantago asiatica* L., *Semen lepidii*, Ephedra, *Romulus Cinnamomi*, *Rheum Palmatum* L., *Morus alba*, root of *Dioscorea polystachya*, *Orchis italica*, *Curculigo orchioides*, *Levisticum officinale*, root of *Asparagus cochinchinensis*, Japanese Honeysuckle, *Ruta graveolens*, *Aster ageratoides* Turcz., and *Typha angustifolia* L.

Chinese Patent Application No. 201510772076.0 discloses a medication for treating spleen phlegm type MPE, comprising *Rheum palmatum* L., *Semen lepidii*, roots of *Curcuma wenyujin*, *Ramulus Cinnamomi*, fruit of Large flower Gardenia, *Iphigenia indica* Kunth, *Prunella vulgaris*, *Codonopsis pilosula*, *Zingiber ojjicinale* Rosc., *Schisandra*

*chinesis*, cattle penis, oriental dodartia herb, *Platycodon grandiflorus, Levisticum officinale*, Ephedra, *Liriope spicata*, fruits of *Arctium lappa* L., Largehead atractylodes rhozome, *Scrophularia ningpoensis* Hemsl., *Acorus tatarinowii* Schott., and licorice.

There are certain methods in treating MPE by Chinese medicine based on five compound medications described above, but their clinical evidences of treating MPE are not sufficient yet. As such, the efficient results of the clinical treatment are hardly achieved due to the defect of five patented medications described above.

SUMMARY OF THE INVENTION

In one aspect of the present disclosure, a pharmaceutical composition for treating malignant pleural effusions (MPE) is provided. The pharmaceutical composition comprises a benzenesulfonamide derivative and a pharmaceutically acceptable excipient.

In one embodiment of the present disclosure, the benzenesulfonamide derivative may be a compound represented by formula (I):

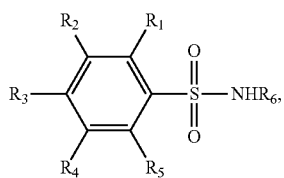

(I)

wherein $R_1$-$R_6$ are each independently selected from the group consisting of H, C1-C6 linear or branched alkyl, C1-C6 linear or branched alkoxy, amino, halo, halo-substituted C1-C6 linear or branched alkyl, and sulfonamide group.

In one embodiment of the present disclosure, the compound of formula (I) may be selected from the group consisting of p-toluenesulfonamide or o-toluenesulfonamide, N-ethyl-p-toluene sulfonamide, N-ethyl-o-toluene sulfonamide, N-cyclohexyl-p-toluene sulfonamide and a combination thereof.

In one embodiment of the present disclosure, the benzenesulfonamide derivative may be present in an amount ranging about 10%-50% by weight. In one embodiment of the present application, the pharmaceutical composition may comprise 10%-50% by weight of the benzenesulfonamide derivative, 10%-40% by weight of PEG-400, 5%-40% by weight of 1,2-propylene glycol, 1%-5% by weight of sebacic acid, 10%-20% by weight of 2-ethyl-1,3-hexanediol, 0%-10% by weight of dimethyl sulfoxide and 0%-10% by weight of ethanol.

In another aspect of the present disclosure, the method for treating malignant pleural effusions is provided. The method comprises administering a therapeutically effective amount of the pharmaceutical composition comprising a benzenesulfonamide derivative to a subject in need thereof.

In one embodiment of the present disclosure, the pharmaceutical composition may be administered to the subject intratumorally, intravenously, subcutaneously, intradermally, orally, intrathecally, intraperitoneally, intranasally, intramuscularly, intrapleuraly, or through nebulization. In another embodiment of the present disclosure, the pharmaceutical composition is administered intrapleuraly to the subject.

In one embodiment of the present disclosure, the subject may be suffering from cancer, such as lung cancer, breast cancer, lymphoma, leukemia, and mesothelioma.

In one embodiment of the present disclosure, the method further comprises administering at least one additional MPE therapy to the subject. The additional MPE therapy may be selected from chest drainage, video-assisted thoracic surgery (VATS), intrathoracic administration, pleural fixation, whole body chemotherapy, radiotherapy, or thermal therapy.

DETAILED DESCRIPTION OF THE PREFERRED EMBODIMENTS OF THE INVENTION

The following examples are used to exemplify the present disclosure. A person of ordinary skills in the art can understand the other advantages of the present disclosure, based on the disclosure of the specification of the present disclosure. The present disclosure can also be implemented or applied as described in different specific examples. It is possible to modify and or alter the examples for carrying out this disclosure without contravening its spirit and scope, for different aspects and applications.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The present disclosure provides a pharmaceutical composition comprising a therapeutically effective amount of benzenesulfonamides as a medicament for MPE and also provides a process for preparing the above composition and a treatment method using the composition.

The pharmaceutical composition of benzenesulfonamides for treating MPE comprises, for example, p-toluenesulfonamide or o-toluenesulfonamide, N-ethyl-p-toluene sulfonamide, N-ethyl-o-toluene sulfonamide, N-cyclohexyl-p-toluene sulfonamide, or other toluenesulfonamides or a combination of two or more in any ratio of different toluenesulfonamides. The monomer of each benzenesulfonamide is in white crystal form.

The benzenesulfonamides may be represented by the following formula (I):

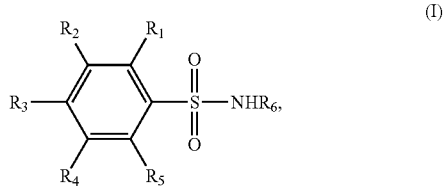

(I)

wherein $R_1$-$R_6$ are each independently selected from the group consisting of H, C1-C6 linear or branched alkyl, C1-C6 linear or branched alkoxy, amino, halo, halo-substituted C1-C6 linear or branched alkyl, and sulfonamide group. Preferably, $R_1$-$R_6$ are each independently H, methyl or ethyl.

The pharmaceutically acceptable excipient included in the pharmaceutical composition of the present disclosure may be conventional pharmaceutical carriers, such as filler, binder, preservative, disintegrating agent, lubricant, suspending agent, wetting agent, solvent, surfactant, acids and flavoring agent.

The binders that are suitable for use in the present disclosure may be starch paste, sorbitol, guar gum, polyvinyl pyrrolidone, cellulose derivatives such as hydroxy propylmethyl cellulose, sodium carboxymethyl cellulose, carbomer (commercially available as carbopols) etc.

The preservatives suitable for use in the present disclosure may be sodium benzoate, methyl paraben, propyl paraben, cresols, etc.

The lubricants that are suitable for use in the present disclosure may be metallic stearates such as magnesium, calcium and sodium stearates, stearic acid, talc, polyethylene glycols, soluble salts such as sodium chloride, sodium benzoate etc.

The wetting agents that are suitable for use in the present disclosure may be glycerol, sorbitol, polypropylene glycol etc.

The flavoring agents that are suitable for use in the present disclosure may be peppermint oil, menthol, lemon oil, orange oil, and cinnamon oil.

Preferably, the pharmaceutically acceptable excipient may be polyethylene glycol (PEG), alkylene glycol, sebacic acid, and/or dimethyl sulfoxide, alcohols. More preferably, the pharmaceutical compositions may comprise the following parts by weight:

Pharmaceutical Composition of Benzenesulfonamides (GNW-601)

| | |
|---|---|
| p-toluenesulfonamide | 10%-50% |
| PEG-400 | 10%-40% |
| 1,2-propylene glycol | 5%-10% |
| Sebacic acid | 1%-5% |
| p-toluenesulfonic acid | 0%-15% |
| 2-ethyl-1,3-hexanediol | 10%-20% |
| Dimethyl sulfoxide | 0-10% |
| Ethanol | 0-10% |

The present disclosure also provides the process for the preparation of pharmaceutical composition.

The process includes: adding and mixing the solvents and adjuvants in a given ratio; heating the mixture to 80° C. to 110° C. with stirring to form a clear oily liquid; gradually adding the sulfa drug with stirring until completely dissolved; filtering and cooling the mixture to obtain the composition of the present disclosure in an oily liquid form (GNW-601).

The process for preparing the injection formulation of GNW-601 may be carried out based on the technique known in the art, for example, by adding adjuvants or and solvents, and further adjusting the mixture to isotonic condition. For example, microporous filters can be used for the step of filtering in the process.

The pharmaceutical composition of benzenesulfonamides may be formulated into a form suitable for parenteral administration, injection, continuous perfusion, sublingual administration, subcutaneous administration or oral administration. In one embodiment of the present disclosure, the pharmaceutical composition may be in a form selected from the group consisting of a formulated to injection, dry powders, tablets, oral liquid, wafers, films, lozenges, capsules, granule, and pill.

For example, GNW-601 for treating MPE can be a solution form and administered to a subject by intramuscular or intrapleural injection or by oral or other routes. GNW-601 also can be other formulation for the oral administration as a medicament for treating MPE. The intrapleural injection dosage for MPE treatment is 3-8 mL/injection (about 990-2640 mg of p-toluenesulfonamide).

The injection dosage for MPE treatment in an adult can be in a range of from about 800 mg to 7,000 mg, such as 825 mg to 6,600 mg, 990 mg to 2,640 mg and 1000 mg to 1800 mg of p-toluenesulfonamide or other benzenesulfonamides.

During the MPE treatment, the therapeutically effective amount of p-toluenesulfonamide or other benzenesulfonamides administered to a subject can be in a range of from about 2475 mg to about 27000 mg.

The present disclosure provides the use of GNW-601 as a medicament for treating MPE.

By the long-term clinical trials, it is proven that the pharmaceutical composition of the present disclosure can improve the clinical symptoms and the life quality of MPE patients. The pharmaceutical composition of the present disclosure is preferably a targeted prescription with the efficacy to the best performance compared to current available medications for treating MPE.

EXAMPLE

Efficacy of MPE treatment by the present disclosure is evaluated in the clinical trials as follows.

Experimental Example 1

The clinical trial was conducted at the First Affiliated Hospital of Guangzhou Medical College from 1992 to 1999. Total 46 cases with MPE were enrolled, there were 16 male and 30 female, aged from 19 to 83 years, and their average age was 54.80±11.62 years. There were 22 cases of squamous cell carcinoma, 18 cases of lung adenocarcinoma, 3 cases of pleural metastasis in breast cancer, and 3 cases of pleural metastasis from primary liver cancer based on histology examination.

Diagnostic criteria: A. patients with advanced cancer, breathing difficulties, chest tightness, and flatness by auscultation, B. chest radiography, B-mode ultrasound, CT scan confirmed MPE, C. pleural effusion, histopathological or cytological examination revealed malignant cells, D. exclusion of other causes of pleural effusion.

Inclusion criteria: A. at least one imaging (CT, X ray, or B-mode ultrasound) showing the quantity of MPE, B. confirmed MPE by histological or cytological diagnosis, C. normal functions of liver, kidney, and blood, D. no interstitial pneumonia or pulmonary fibrosis, E. informed consent forms signed by patients or their family members.

Exclusion criteria: A. end-stage patients with cachexia and severe hypoalbuminemia; unable to complete the treatment, B. basal treatment combined with other anti-cancer therapies, C. other causes of pleural effusions such as infections or cardiopathy, D. pregnant women, or mental disorders, or those not following the treatment scheme.

Meeting at least one of the following criteria should be withdrawn from the clinical trial: A. rapidly deterioration or death during trial, B. patient condition or patient himself requesting stop of treatment before completion of a treatment course, C. those poorly complying with scale fill, D. not meeting inclusion criteria after enrollment.

Treatment methods: before GNW-601 administration, remove MPE was performed with the intrapleural injection needle one or two times (800-1400 mL per day) when necessary. GNW-601 was intrapleuraly injected 3-8 mL (about 990-2,640 mg of p-toluenesulfonamide). The pleural effusion suction and GNW-601 injection process was repeated when the effusion grew back to significant amount again for some of the patients.

Response Evaluation Criteria:

CT, X ray, or B-mode ultrasound examinations were performed before and after the administrations. Complete response (CR): pleural effusion completely disappeared; partial response (PR): pleural effusion significantly reduced (≥50% reduction); stable disease (SD): pleural effusion decreased without increasing trend; progress disease (PD): no reduction or increase in pleural effusion. The total efficacy: CR+PR.

Clinical evaluation included guiding patients to fill in case report forms based on the severity of symptoms (dyspnea, cough, chest pain, weight loss, coughing up blood and sputum, lassitude, loss of appetite, etc.)

Adverse reactions were reported according to the grading standards of common adverse reactions of CTCAE grading (Common Terminology Criteria for Adverse Events).

Observation Methods:

Outcome measures included: A. general recording items, B. relieved conditions of pleural effusion verified by CT, X ray, or B-mode ultrasound, C. the changes in the life quality, D. adverse reactions.

The following results were revealed in 46 patients:

Term effects: complete response (CR) 24 cases, partial response (PR) 9 cases, stable disease (SD) 7 cases, progress disease (PD) 6 cases; the total efficacy is 71.7% (33/46).

Adverse reactions: Main side effects included drowsiness, fatigue and loss of appetite. Ten patients had fever (37.5° C. to 38° C.). All symptoms disappeared within 12 hours. None of the usual side effects, such as pain, nausea and hair loss, was observed. There were no observed abnormalities in hematology and renal functions during and after treatment.

Conclusions: The pharmaceutical composition of the present disclosure can treat MPE, and improves the life quality and clinical symptoms of MPE patients. No significant increase in adverse reactions was observed.

Experimental Example 2

The clinical trial was conducted at Beijing Cancer Hospital, The First Affiliated Hospital of Guangzhou Medical University, Zhongshan Hospital affiliated to Fudan University, and The People's Hospital of GaoZhou, from June 2005 to May 2007. Total 26 patients with MPE were enrolled, there were 12 male and 14 female, aged from 42 to 89 years, and their average age was 64 years. This trial followed the Declaration of Helsinki (Rev. 1996) and the relevant ethics principles in Good Clinical Practice, and execute relevant provisions of SFDA. This protocol was executed after approved by the Ethics Committee.

Inclusion criteria: A. patients with MPE clearly diagnosed by histologic examination (clear cytological diagnosis for subjects with MPE), B. patients aged 18-75 years, C. for females, they must be menopause for 1 year or have surgical sterilization; or abstinence or have their partner contraception; or adopt oral, implanted or injected contraceptives or other permitted contraceptives (including intrauterine device, female condom, diaphragm with spermicide, cervical cap, or condom for their partners); women of childbearing age must have negative pregnancy test result when enrolled, D. ECOG score of 0 to 3, E. life expectancy is more than 3 months, F. able to tolerate local drug injection, G. Sufficient function in bone marrow, kidney and liver (White blood count (WBC) ≥3000/mm³; Platelet count ≥75,000/mm³; Serum creatinine ≥2.0 mg/dL, or creatinine clearance ≥60 mL/min; Total bilirubin ≥2.0 mg/dL; SGOT and SGPT ≥2.5×ULN; Alkaline phosphatase ≥5× ULN), H. HIV test must be negative, G. able to understand and comply with the protocol, and sign the Informed Consent Form.

Exclusion criteria: A. there is any important structure such as blood vessels or nerves around the lesions so that it is not suitable for local injection, B. patients with small cell lung cancer, C. patients with serious concomitant disease, including active and uncontrollable infection or serious cardiac, hepatic, renal or hematological failure, D. pregnant or breast lactating female, E. known allergy to the treating drugs in the trial or relevant compounds, F. patient who had received systemic anti-tumor treatment for malignant tumor within 4 weeks before enrollment, or who had received Nitrosourea or Mitomycin-C for systemic treatment within 6 weeks, G. patients who had participate in other clinical trial with unapproved test drug or methods within 4 weeks before enrollment, H. patients with history of other malignant tumors, unless it is cured and stay relieved for more than 2 years, I. patients with history of homo-transplantation or hetero-transplantation, J. patients received radiotherapy for local disease within 4 weeks before enrollment, K. patients with any other life-threatening complications, L. patients are unwilling to comply with the procedures stipulated in the protocol, or unwilling to completely cooperate with investigator, M. other reasonable exclusion criteria considered by investigator.

Meeting at least one of the following criteria should be withdrawn from the clinical trial: A. after the treatment of at least 2 weeks, imaging examination shows most MPE obviously disappeared or patients with extensive pleural adhesion, B. patients are intolerable adverse events or serious adverse events, C. the subject asks for withdrawal, D. required by sponsor, E. treatment duration reaches 6 weeks, F. other reasons considered by the investigator.

Treatment methods: after routine preoperative preparation and local anesthesia, the effusion was drawn out through transthoracic puncture guided by B-mode ultrasound. After the drainage of pleural effusion (as thoroughly as possible), the original needle was retained for perfusing drug into pleural cavity with a new syringe with GNW-601. The patients were advised to lie on the back after drug perfusion into pleural cavity, and assisted to rotate to make the drug distributed uniformly within the pleural cavity (at least once every 30 minutes). GNW-601 was intrapleuraly injected 2.5-20 mL per daily injection (about 825-6,600 mg of p-toluenesulfonamide), 7.5-90 mL in total during the whole treatment period. Patients were conducted for 2-8 times of injections within 1-24 days with the interval 1-13 days.

Response Evaluation Criteria:

During screening period, withdrawal period and/or follow-up period, the imaging examination (B-mode ultrasound, CT, or chest radiography and other appropriate imaging evaluation methods) was performed to evaluate the volume of pleural effusion. The response was evaluated based on effusion volume. Complete response (CR): disappearance of pleural effusion; partial response (PR): at least >50% decrease in pleural effusion, compared to baseline; stable disease (SD): neither sufficient decrease to qualify for PR nor sufficient increase to qualify for PD, compares to the pleural effusion at baseline; progress disease (PD): at least >25% increase in pleural effusion, compared to baseline. The total efficacy: CR+PR.

Outcome measures included: A. relieved conditions of pleural effusion (the volume of pleural effusion measured by B-mode ultrasound, CT, or chest radiography and other appropriate imaging evaluation methods), B. adverse reactions. Adverse reactions were reported according to the grading standards of common adverse reactions of CTCAE grading (Common Terminology Criteria for Adverse Events).

Treatment results: the following results were revealed in 23 out of 26 total enrolled patients (relieved conditions of pleural effusion in 3 patients not determined):

Term effects: complete response (CR) 0 case, partial response (PR) 21 cases, stable disease (SD) 1 case, progress disease (PD) 1 case; the total efficacy is 95.65% ($^{22}/_{23}$).

Adverse reactions: main side effects included chest pain ($^{5}/_{26}$, 19.23%), chest distress ($^{3}/_{26}$, 11.53%), dizziness ($^{2}/_{26}$, 7.69%), and palpitations ($^{2}/_{26}$, 7.69%).

Conclusions: The pharmaceutical composition of the present disclosure can treat MPE patients. No significant increase in adverse reactions was observed.

What is claimed is:

1. A method for treating a malignant pleural effusion (MPE), comprising
administering a pharmaceutical composition comprising a benzenesulfonamide derivative and a pharmaceutically acceptable excipient thereof to a subject in need thereof, wherein the benzenesulfonamide derivative is a compound represented by formula (I):

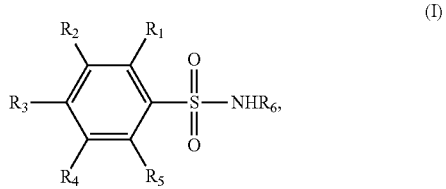

and
wherein $R_1$ to $R_6$ are each independently selected from the group consisting of H, C1-C6 linear or branched alkyl, C1-C6 linear or branched alkoxy, amino, halo, halo-substituted C1-C6 linear or branched alkyl, and sulfonamide group; and
administering at least one additional MPE therapy, wherein the at least one additional MPE therapy is chest drainage;
wherein the benzenesulfonamide derivative in the pharmaceutical composition is administered to the subject in a therapeutically effective amount of from about 825 mg to about 6600 mg per day.

2. The method according to claim 1, wherein the benzenesulfonamide derivative in the pharmaceutical composition is administered to the subject in a therapeutically effective amount of from about 990 mg to about 2640 mg per day.

3. The method according to claim 1, wherein the benzenesulfonamide derivative in the pharmaceutical composition is administered to the subject in a therapeutically effective amount of from about 1000 mg to about 1800 mg per day.

4. The method according to claim 1, wherein the therapeutically effective amount of the benzenesulfonamide derivative administered to the subject during the treatment is in a range of from about 2475 mg to about 27000 mg.

5. The method according to claim 1, wherein the pharmaceutical composition is administered to the subject intratumorally, intravenously, subcutaneously, intradermally, orally, intrathecally, intraperitoneally, intranasally, intramuscularly, intrapleuraly, or through nebulization.

6. The method according to claim 1, wherein the subject is suffering from cancer.

7. The method according to claim 6, wherein the cancer is at least one selected from the group consisting of lung cancer, breast cancer, lymphoma, leukemia, and mesothelioma.

8. The method according to claim 1, further comprising administering at least one additional malignant pleural effusion (MPE) therapy to the subject; wherein the additional MPE therapy is video-assisted thoracic surgery (VATS), intrathoracic administration, pleural fixation, whole body chemotherapy, radiotherapy, or thermal therapy.

9. The method according to claim 1, wherein the compound of formula (I) is selected from the group consisting of p-toluenesulfonamide, o-toluenesulfonamide, N-ethyl-p-toluene sulfonamide, N-ethyl-o-toluene sulfonamide, N-cyclohexyl-p-toluene sulfonamide and a combination thereof.

10. The method according to claim 1, wherein the benzenesulfonamide derivative is present in the pharmaceutical composition in an amount ranging from about 10% to about 50% by weight.

11. The method according to claim 1, wherein the pharmaceutical composition further comprises at least one of 10%-40% by weight of PEG-400, 5%-10% by weight of 1,2-propylene glycol, 1%-5% by weight of sebacic acid, 10%-20% by weight of 2-ethyl-1,3-hexanediol, 0%-10% by weight of dimethyl sulfoxide and 0%-10% by weight of ethanol.

* * * * *